United States Patent [19]

Massa

[11] 4,342,229
[45] Aug. 3, 1982

[54] APPARATUS AND METHOD FOR THE NON-DESTRUCTIVE TESTING OF THE PHYSICAL INTEGRITY OF A STRUCTURAL PART

[75] Inventor: Frank Massa, Hingham, Mass.

[73] Assignee: The Stoneleigh Trust, Cohasset, Mass. ; Fred M. Dellorfano, Jr. and Donald P. Massa, Trustees

[21] Appl. No.: 180,680

[22] Filed: Aug. 25, 1980

[51] Int. Cl.³ ............................ G01H 1/00; G01H 9/00
[52] U.S. Cl. ............................................ 73/579; 73/583
[58] Field of Search ................ 73/598, 579, 583, 602, 73/658

[56] References Cited

U.S. PATENT DOCUMENTS

| | | | |
|---|---|---|---|
| 2,178,252 | 10/1939 | Forster | 73/579 |
| 3,019,387 | 1/1962 | Rowe | 73/579 |
| 3,043,132 | 7/1962 | Schubring | 73/579 |
| 3,097,523 | 7/1963 | Diamond | 73/584 |
| 3,106,838 | 10/1963 | Crooks | 73/588 |
| 3,345,861 | 10/1967 | Heath | 73/579 |
| 3,550,434 | 12/1970 | Schroeer et al. | 73/579 |
| 3,580,056 | 5/1971 | Warner | 73/579 |
| 4,041,774 | 8/1977 | Morris et al. | 73/610 |
| 4,212,201 | 7/1980 | Hirsch et al. | 73/579 |
| 4,318,302 | 3/1982 | Choi | 73/579 |

OTHER PUBLICATIONS

J. M. Carson and J. L. Rose, An Ultrasonic Nondestructive Test Procedure for the Early Detection of Fatigue Damage and the Prediction of Remaining Life, Apr. 1980 research supplement.

Primary Examiner—Anthony V. Ciarlante
Assistant Examiner—David V. Carlson

[57] ABSTRACT

A test procedure and test apparatus is described for measuring the degradation in the physical integrity of a structural part by measuring the rate of decay of the amplitude of vibration of the part after it has been set into vibration at its free resonant frequency mode. The presence of invisible imperfections in the part such as may occur as a result of metal fatigue or from the development of tiny flaws or cracks will cause an increase in the rate of decay of the amplitude of vibration of the part. By making periodic measurements of the rate of decay of a structural part which is used in a critical highly stressed application subject to vibration such as a jet engine mount, the periodic degradation due to fatigue can be determined and the part is removed from service at a safe period before the degradation reaches an unsafe limit.

17 Claims, 4 Drawing Figures

APPARATUS AND METHOD FOR THE NON-DESTRUCTIVE TESTING OF THE PHYSICAL INTEGRITY OF A STRUCTURAL PART

This invention is concerned with improved means for the non-destructive testing of structural parts and particularly with a means for measuring the degradation of the physical integrity of a structural part such as occurs when invisible flaws or cracks develop in the structural member. When highly stressed structural members are used in applications subject to vibration, it is important to make certain that each member is free of structural imperfections before it is installed and also that it remains free of fatigue deterioration throughout its period of use so that the structural safety of the member will not be compromised. When a structural part is used in a critical application such as in jet aircraft engine mounts, the ncessity for having a means for periodically detecting the occurrence of any degradation in the physical integrity of the structural part is obvious.

A conventional prior art method for detecting surface cracks in a structural part is to examine the part under ultra-violet light after coating the surface with a liquid which will fluoresce when illuminated. The liquid penetrates into the surface cracks and the cracks glow when illuminated with the ultra-violet light. Another conventional method for examining a part for the presence of internal flaws is to X-ray the part. Both these prior art methods have limitations in that very small cracks and flaws are not readily detected and considerable risk remains because imperfect parts with small or hidden flaws may not be discovered for rejection. Several serious accidents have occurred due to jet engines falling off airplanes because of failure of the engine mounts due to metal fatigue. This invention achieves considerable improvement over the prior art methods of non-destructive testing and provides a new apparatus and method for detecting the presence of imperfections in a structural part, which are undetectable by prior art procedures.

The test procedure and the test apparatus to be described for measuring the physical integrity of a structural member measures the rate of decay of the amplitude of vibration of the structural part after it has been set into vibration at its free resonant frequency mode. The presence of imperfections such as tiny cracks, or the development of metal fatigue will result in an increased rate of decay of the amplitude of vibration of the part under test. Thus, by making a quantitative periodic measurement of the rate of decay of a structural part as taught by this invention, any increase in the rate of decay will be an indication of the amount of degradation which has taken place in the mechanical integrity of the part.

The primary object of this invention is to measure the mechanical integrity of a structural member by measuring the rate of decay of the amplitude of vibration of the structural member after it has been set into vibration at a free resonant frequency mode.

Another object of the invention is to measure the rate of decay of the amplitude of vibration of a structural part after it has been set into vibration at its free resonant frequency mode, and to compare the measured decay rate with the decay rate of a standard reference part which has been selected as being free from all flaws.

A further object of the invention is to segregate the tested parts into quality groups ranging from perfect to poor, based on the amount of deviation in the measured decay rate of the amplitude of vibration of a part compared to the decay rate measured for the reference standard part.

Still another object of this invention is to provide a test apparatus that will indicate the decay rate of a freely vibrating mechanical part on the screen of an oscilloscope in which the decrease in amplitude of the vibration is displayed on a logarithmic scale as a linear function of time, thereby providing a straight line plot on the oscilloscope whose slope is a direct measure of the logarithmic rate of decay of the vibration.

Another object of the invention is to provide a digital readout on the test apparatus that will indicate the slope of the decay characteristic of the part under test in logarithmic units per unit of time such as, for example, in decibels per second.

Still another object of the invention is to provide a method for periodically testing the physical integrity of a structural member which is subject to metal fatigue during its use by periodically measuring the rate of decay of the amplitude of vibration of the structural member after it has been set into vibration at a free resonant frequency mode. Any change in the periodically measured decay rate is a direct indication of the amount of degration in the physical integrity of the part and a comparison of the periodic decay rate measurement against an experimentally established maximum acceptable decay rate will establish a guide for determining when the part should be discarded from further use.

Another object of the invention is to provide a method for using the invention to establish a correlation between the physical integrity of a structural part and the measured rate of decay of the amplitude of vibration of the structural member after it has been set into vibration at a free resonant frequency mode.

This invention contemplates other objects, features and advantages that will become more fully apparent from the following description taken in conjunction with the accompanying drawings in which.

Figure 1:
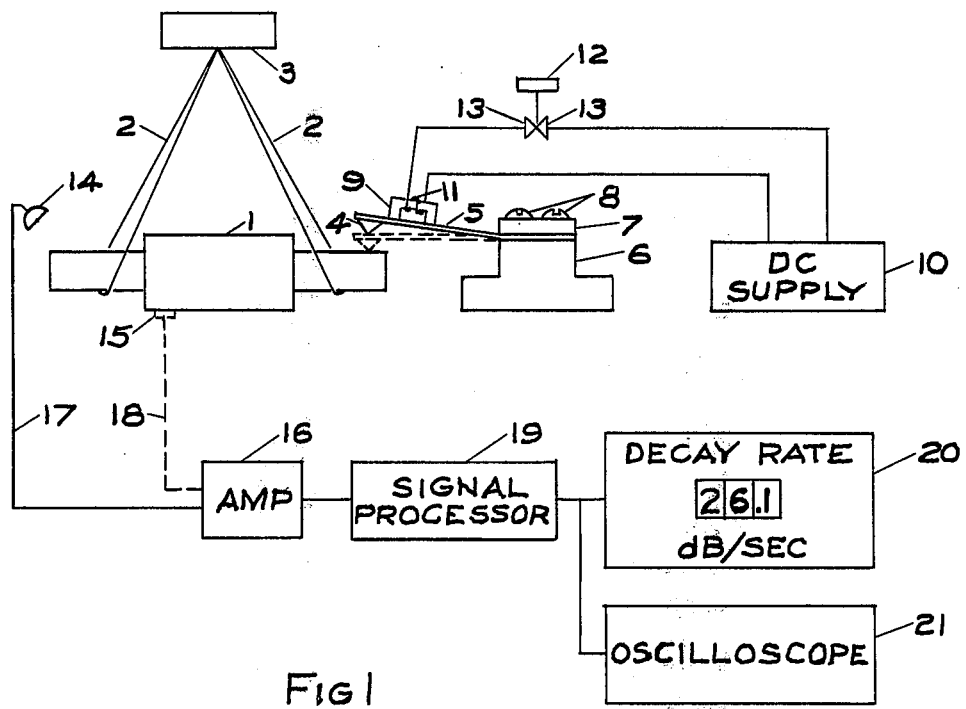
FIG. 1 is a schematic representation of one preferred embodiment of my invention.

Referring more specifically to the figures, the reference character 1 illustrates a structural part being tested in accordance with the teachings of this invention. The part is freely suspended by the support members 2 which are attached to a rigid beam 3. The supports 2 may comprise any suitable loss-free suspension members such as thin-gage, high-tensile steel wires, or compliant cords made from low-loss material such as polybutadience rubber. The method of suspension illustrated in FIG. 1 is only one of several types that may be used. For example, the part under test could be mounted on two knife edge supports which are preferably located near nodal points of the vibrating structure. The preferred location of the suspension points may be easily determined by moving the points of suspension until the measured rate of decay of the amplitude of vibration is a minimum. Another method of suspension is to support the part on a loss-free soft pad of sponge rubber-like material. This type of mounting will be suitable for relatively light weight structures, but would be less practical for use with massive structures.

An illustration of one type of impulse force generator that is suitable for setting the structural part under test into vibration utilizes a rigid hammer tip member 2, which is preferably made from hardened steel, attached to one end of a flat leaf spring member 5 which is made of magnetic material. The other end of the spring member 5 is clamped to a rigid base member 6 by means of the clamping plate 7 and the screws 8. An electromagnet 9 holds the spring member 5 in the raised position as shown by the solid line in FIG. 1 by virtue of the dc current which passes from the dc supply 10 through the magnet winding 11. When the pushbutton switch 12 is momentarily pressed, the switch contacts 13 are spread open for an instant which releases the magnetic hold on the spring member 5, and the hammer tip 4 strikes the structural member 1 as illustrated by the dotted position of the spring member 5. When the hammer tip rebounds after striking, the switch contacts 13 have already been closed so that the spring member 5 is automatically held by the magnetized electromagnet 9 as illustrated by the solid line position. The mechanical impulse strike cycle can be repeated by again pressing the switch 12 momentarily as desired. It is obvious that the impulse force may be applied by employing any other type of trip mechanism that is well known in the art. A manually applied hammer blow is also suitable as a means for imparting an impulse force to the structural member under test, especially if the part is large.

After the impulse force is applied to the structural part, the part will be set into vibration at its free resonant frequency mode. The vibrational amplitude of the vibrating structure is converted to an electrical signal by a suitable transducer, such as a microphone 14 which picks up the sound vibrations generated by the vibrating structure 1 or, alternately, an accelerometer 15 may be attached to the surface of the structure under test as illustrated in FIG. 1. If an accelerometer is used, its weight must be negligible compared to the weight of the structure 1. In most cases, the microphone will be the preferable transducer because it requires no mechanical attachment to the vibrating structure under test.

Figure 2:
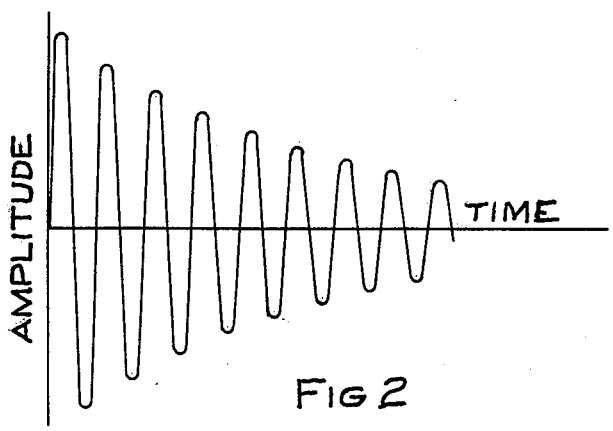
FIG. 2 is a plot showing the rate of decay of the amplitude of vibration vs. time of the suspended part shown in FIG. 1 after it has been set into vibration by an impulse force.

The output from the transducer is connected to the input of the amplifier 16. The connection from the microphone 14 is illustrated by the solid line 17. A dotted line 18 illustrates the connection if an accelerometer 15 is used as the transducer instead of the microphone. The amplifier output signal which represents the amplitude of vibration of the structure 1 as a function of time is an exponentially decaying sine wave as shown in FIG. 2. The output signal from amplifier 16 is applied to the input of the signal processor 19 which includes a peak detector and a microprocessor for measuring the rate of decay of the peak values of the sine wave signals shown in FIG. 2 as a function time. The microprocessor will preferably compute the logarithm of the peak amplitude of the signal and a digital meter 20 will be operated by the microprocessor to display the decay rate of the logarithm of the peak amplitude of the signal in convenient units such as, for example, dB/sec as illustrated in FIG. 1. The output from the signal processor 19 is also connected to an oscilloscope 21, which preferably has a storage display tube which holds the decay curve on the screen permanently for observation until erased.

Figure 3:
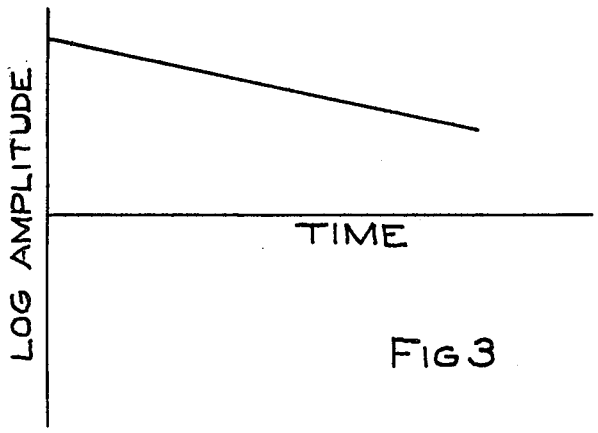
FIG. 3 is a plot of the logarithm of the peak value of the amplitude of the signal plotted in FIG. 2.

FIG. 3 illustrates the appearance of the logarithmic decay characteristic of the vibrating structural member on the oscilloscope screen. The slope of the decay characteristic in FIG. 3 is a direct measure of the integrity of the part under test. An increase in the slope will occur as flaws develop in the part.

Figure 4:
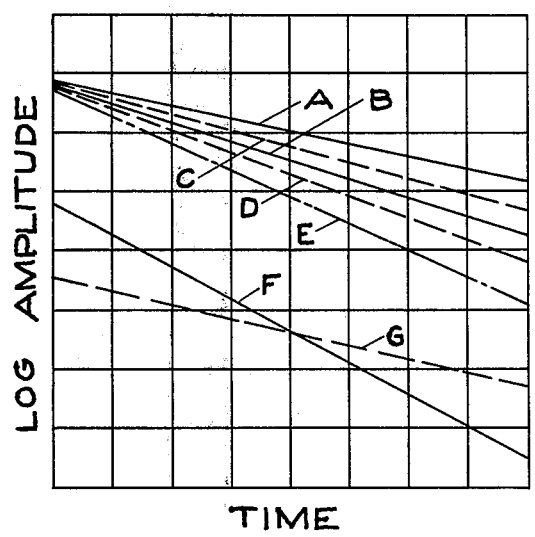
FIG. 4 is an enlarged view of the oscilloscope screen of FIG. 1 showing the appearance of various plots of the logarithmic rates of decay of the amplitude of vibration of a structural part as illustrated in FIG. 3 for different degrees of degradation of the mechanical integrity of the part.

FIG. 4 illustrates how the decay characteristics will appear on the oscilloscope screen for various parts being measured. Curve A represents the decay characteristic of a mechanically perfect structural part which is selected from among several "perfect" parts which have been judged to be without flaws as determined by conventional visual and X-ray examination. The various "perfect" parts when tested by the inventive apparatus might display oscillograms whose logarithmic decay characteristics vary between Curve A and Curve B. In order to determine what maximum rate of decay should be established as the minimum acceptable quality for a newly manufactured part, several "perfect" parts selected by prior art test procedures and having rate of decay slopes that range between A and C by the inventive test procedure will be subjected to accelerated fatigue life tests by subjecting the parts to controlled high frequency fixed amplitude vibration. At periodic intervals, the decay rate for each part will be recorded in dB/sec while the fatigue life tests go on until the fatigue limit is reached for all of the parts. During this life test, data will have been accumulated for each part showing the number of hours of remaining life before the fatigue limit is reached for each part as a function of the measured periodic decay rate observed for each part during the fatigue test period. From these data a conservative limit can be established for the maximum measured rate of decay that can be permitted for the acceptance of a new part and also what maximum decay rate can be permitted during the periodic testing periods while the part is in service, at which time the part is removed from service. For example, new structural parts whose measured rates of decay fall below Curve C in FIG. 4 will be rejected at the time of manufacture. Assuming that Curve E represents the last measured slope of the decay characteristic before fatigue failure occurs, some intermediate slope D, which is reached at a time safely in advance of the time required to reach the fatigue limit as represented by Curve E, can be established for the condition when it becomes necessary to remove the structural part from service during the periodic test measurements.

Curves F and G in FIG. 4 illustrate a dual type of decay characteristic that may occur for some complex part in which one section has a different rate of decay than another section of the part. The different sections could also resonate at different frequencies. In such a case, the rate of decay of the amplitude of vibration of the complex structure might start as Curve F (which is the rate of decay of one portion of the structural member) and continue as Curve G (which is the rate of decay of another portion of the structure member). In this case, the rate of decay in dB/sec can be measured for both slopes and the permissible changes in rates of decay for both slopes would have to be established by running fatigue life tests as described above and the part is removed from service whenever either slope reaches the maximum permissible rate of decay.

Details of the amplifier, signal processor, microcomputer circuits and other electronic circuits have not been shown because they are well known to any electronic or computer engineer skilled in the art and the circuit details are not part of this invention. This invention is in the system which comprises the apparatus for making the measurements described and in the method of using the inventive apparatus to establish the physical integrity of a structureal part. The inventive apparatus measures the rate of decay of the amplitude of vibration of the part after it is excited by an impulse force into a resonant frequency mode. The measured increase in the rate of decay at periodic intervals is an indication of the degree of degradation taking place in structural parts. When the rate of decay reaches the maximum permissible rate, as established by the experimental fatigue life test data herein described, which is safely ahead of the time when the fatigue limit for the structural member will occur, the structural member is removed from service.

While a few specific embodiments of the present invention have been shown and described, it should be understood that various additional modifications and alternative constructions may be made without departing from the true spirit and scope of the invention. Therefore, the appended claims are intended to cover all such equivalent alternative constructions that fall within their true spirit and scope.

I claim:

1. In combination in an apparatus for measuring the degradation of the physical integrity of a structural part, such as may occur from the presence of invisible flaws in the structural material or from vibrational fatigue of the structural material during the operational use of the structural part, support means for holding said structural part, said support means characterized in that it presents negligible resistance to the free natural vibration of said structural part, force excitation means associated with said supported structural part, said force excitation means characterized in that an impulse force of short duration may be imparted to said structural part upon command, said impulse force characterized in that it is of sufficient magnitude to excite said structural part into a free resonant mode of vibration, transducer means for converting the amplitude of vibration of said freely vibrating structural part to an electrical signal, means for continuously measuring the decaying amplitude of said electrical signal over a specified period of time of sufficient duration to include a plurality of oscillatory cycles of said vibrating structural part immediately following the excitation of said freely suspended structural part by said impulse force, and indicator means for indicating the logarithm of said measured decaying amplitude over said specified period of time, whereby said logarithm of said measured decaying amplitude is an indication of the physical integrity of said vibrating structural part.

2. The invention in claim 1 characterized in that said transducer means is an accelerometer.

3. The invention in claim 1 characterized in that said transducer means is a microphone.

4. The invention in claim 1 characterized in that said means for measuring said decaying amplitude of said electrical signal includes a logarithmic amplifier in which the output signal level is proportional to the logarithm of the input signal level.

5. The invention in claim 1 characterized in that the continuous measurement of the decaying amplitude of said electrical signal includes the measurement of each successive amplitude of vibration of the decaying oscillatory vibrations of said vibrating structural part over said specified period of time.

6. The invention in claim 1 characterized in that said indicator means includes means responsive to the continuously measured decaying peak amplitude of vibration of the structural part during said specified period of time.

7. The invention in claim 6 further characterized in that the continuous measurement of the decaying peak amplitude of vibration of the structural part includes the measurement of each successive peak amplitude of vibration of the structural part during said specified period of time.

8. The invention in claim 1 characterized in that said indicator means includes means responsive to the logarithm of the continuously measured decaying peak amplitude of vibration of the structural part during said specified period of time.

9. The invention in claim 8 further characterized in that said indicator means includes means for indicating said logarithmic measurements in decibels per second.

10. The invention in claim 8 further characterized in that said indicator means includes an oscilloscope and still further characterized in that said oscilloscope displays the logarithm of the decaying peak signal amplitude as a function of time.

11. The invention in claim 8 further characterized in that the continuous measurement of the decaying peak amplitude of vibration of the structural part includes the measurement of each successive peak amplitude of vibration of the structural part during said specified period of time.

12. The invention in claim 10 further characterized in that the oscilloscope includes a storage tube whereby the oscilloscope display remains fixed on the oscilloscope screen to permit accurate measurement of the logarithmic decay rate of said peak signal amplitude.

13. The invention in claim 10 further characterized in that said indicator means includes a digital display which indicates the slope of the logarithmic decay rate of the vibrating part under test.

14. The invention in claim 7 further characterized in that said indicator means includes a digital display which indicates the slope of the logarithmic decay rate in decibels per second.

15. A method for the non-destructive testing of the degradation of the physical integrity of a structural part, such as may be caused by the presence of invisible flaws in the structural part, which includes the following steps:

1. suspend the structural part with a non-restrictive suspension system,
2. impart an impulse force of short duration to the suspended part of sufficient magnitude to set the part into vibration at a free resonant frequency mode,
3. continuously measure the decaying amplitude of vibration of the suspended vibrating part over a specified period of time of sufficient duration to include a plurality of oscillatory cycles of said vibrating part immediately following the excitation of said structural part by said impulse force,
4. compare the logarithm of the measured rate of decay of the amplitude of vibration with a specified maximum logarithm of the rate of decay which has been established as a limit beyond which the structural part is considered to be defective, 5. reject the part when the logarithm of the measured rate of decay of the amplitude of vibration equals or exceeds the logarithm of the maximum specified rate of decay.

16. The method for establishing an empirical relationship between the physical integrity of a structural member and the rate of decay of the amplitude of vibration of the structural member after it has been set into vibration at a free resonant frequency mode, which includes the following steps:
   1. place a selected structural member which is free from flaws under fatigue life test by subjecting the member to a controlled high frequency cyclic stress,
   2. at periodic intervals interrupt the fatigue life test and continuously measure the decaying amplitude and logarithm of vibration of the structural member for a specified period of time of sufficient duration to include a plurality of oscillatory cycles of said vibrating member immediately following the excitation of the structural member by an impulse force to set it into vibration at a free resonant frequency mode,
   3. continue the life test and periodic vibrational amplitude measurements until fatigue failure occurs for the structural member,
   4. correlate the periodic logarithm of the measurements of the decaying amplitude of vibration of the structural member with the total time of exposure of the structural member to the fatigue lift test.

17. The invention in claim 16 and the additional step:
   5. establish a maximum limit for the rate of decay of the amplitude of vibration of the structural member which corresponds to the maximum permissible degradation of the structural integrity of the structural part which is safely ahead of the time at which fatigue failure occurs, and at which point the part should be removed from service.

* * * * *